US010410655B2

United States Patent
Malur Srinivasan et al.

(10) Patent No.: US 10,410,655 B2
(45) Date of Patent: Sep. 10, 2019

(54) ESTIMATING EXPERIENCED EMOTIONS

(71) Applicant: FUJITSU LIMITED, Kawasaki-shi, Kanagawa (JP)

(72) Inventors: Ramya Malur Srinivasan, Sunnyvale, CA (US); Ajay Chander, San Francisco, CA (US)

(73) Assignee: FUJITSU LIMITED, Kawasaki (JP)

( * ) Notice: Subject to any disclaimer, the term of this patent is extended or adjusted under 35 U.S.C. 154(b) by 45 days.

(21) Appl. No.: 15/846,086

(22) Filed: Dec. 18, 2017

(65) Prior Publication Data
US 2019/0088270 A1   Mar. 21, 2019

Related U.S. Application Data

(60) Provisional application No. 62/560,101, filed on Sep. 18, 2017.

(51) Int. Cl.
*G10L 25/63* (2013.01)
*G10L 17/26* (2013.01)
(Continued)

(52) U.S. Cl.
CPC ............... *G10L 25/63* (2013.01); *A61B 5/16* (2013.01); *A61B 5/7264* (2013.01);
(Continued)

(58) Field of Classification Search
CPC ........... G10L 25/63; G10L 17/26; A61B 5/16; A61B 5/7264; G06K 9/00288; G06K 9/00302
See application file for complete search history.

(56) References Cited

U.S. PATENT DOCUMENTS 10,244,975 B2 * 4/2019 Wrenn ................. A61B 5/4088
2008/0269958 A1 * 10/2008 Filev ..................... B60W 50/10
701/1
(Continued)

OTHER PUBLICATIONS

Use of Sentiment Analysis for Capturing Patient Experience From Free-Text Comments Posted Online; 2013 (Year: 2013).*
(Continued)

*Primary Examiner* — Mohammad K Islam
(74) *Attorney, Agent, or Firm* — Maschoff Brennan

(57) ABSTRACT

A method may include obtaining data input including one or more words. The method may include determining a set of expressed emotions and a set of expressed emotion probabilities based on the one or more words. The method may include obtaining a set of likelihood probabilities. Each likelihood probability may correspond to a conditional probability of an expressed emotion given an experienced emotion of a group of experienced emotions. The method may include determining a set of experienced emotions of the group of experienced emotions and a set of experienced emotion probabilities based on the set of expressed emotion probabilities and the set of likelihood probabilities. The method may include selecting an experienced emotion of the set of experienced emotions based on the selected experienced emotion corresponding to the highest experienced emotion probability of the set of experienced emotion probabilities. The method may include presenting the selected experienced emotion.

20 Claims, 7 Drawing Sheets

(51) Int. Cl.
*A61B 5/16* (2006.01)
*G06K 9/00* (2006.01)
*A61B 5/00* (2006.01)

(52) U.S. Cl.
CPC ..... *G06K 9/00288* (2013.01); *G06K 9/00302* (2013.01); *G10L 17/26* (2013.01); *A61B 5/0077* (2013.01)

(56) References Cited

U.S. PATENT DOCUMENTS

| | | | |
|---|---|---|---|
| 2016/0317074 A1* | 11/2016 | Kawai | G16H 50/30 |
| 2017/0031598 A1 | 2/2017 | Jayaraman et al. | |
| 2017/0323013 A1* | 11/2017 | Morimoto | G06F 16/353 |
| 2017/0344713 A1* | 11/2017 | Riistama | G06K 9/00892 |
| 2018/0047391 A1* | 2/2018 | Baik | G10L 15/22 |
| 2018/0132776 A1* | 5/2018 | Flickinger | A61B 5/6826 |
| 2018/0150751 A1* | 5/2018 | Lee | G06N 7/005 |
| 2018/0277093 A1* | 9/2018 | Carr | G06F 3/011 |
| 2018/0286429 A1* | 10/2018 | Bostick | G06F 17/2775 |

OTHER PUBLICATIONS

Duyu Tang, Furu Wei, Bing Qin, Nan Yang, Ting Liu, Ming Zhou, Sentiment Embeddings with Applications to Sentiment Analysis, IEEE Transactions on Knowledge and Data Engineering (vol. 28, Issue: 2, Feb. 1, 2016), Oct. 12, 2016.
Medhat et al, Sentiment analysis algorithms and applications: A survey, Ain Shams Engineering Journal, Apr. 19, 2014.
R Socher et al, Recursive deep models for semantic compositionality over sentiment treebank, EMNLP, 2013. (Jul. 5, 2013).
Glorot et al, Domain Adaptation for large scale sentiment classification—A Deep Learning Approach, ICML 2011. (Jun. 28, 2011).
Santos, et. Al. Deep Convolutional Neural Networks for Sentiment Analysis of Short Texts, CoLING Aug. 23, 2014.
Wager etal, A Bayesian Model of Category-Specific Emotional Brain Responses, PLOS, Apr. 8, 2015.
Ong, etal, Affective cognition: Exploring lay theories of emotion, Cognition, Oct. 2015.
Dricu et al, Perceiving emotional expressions in others: Activation likelihood estimation meta-analyses of explicit evaluation, passive perception and incidental perception of emotions, Neuroscience and Biobehavioral Review, Oct. 24, 2016.
Ochs et al, Intelligent Expressions of Emotions, ACII 2005 (Oct. 22, 2005).
Kron et al, How are you feeling? Revisiting the quantification of emotional qualia, Psychological Science, Jul. 3, 2011.
Mikilov et al, Distributed Representations of Words and Phrases and their Compositionality, NIPS, 2013 (Dec. 5, 2013).

* cited by examiner

ESTIMATING EXPERIENCED EMOTIONS

FIELD

The embodiments discussed herein are related to estimating experienced emotions.

BACKGROUND

Individuals may interact with others through conversational user interfaces. Humans may interact with artificial intelligence chat programs or other humans. Advances in artificial intelligence have enabled dramatic changes in the way individuals interact with conversational user interfaces. It can be difficult for a human or a programmed response to understand the emotions behind the messages an individual is conveying through the messages that are sent.

The subject matter claimed herein is not limited to embodiments that solve any disadvantages or that operate only in environments such as those described above. Rather, this background is only provided to illustrate one example technology area where some embodiments described herein may be practiced.

SUMMARY

According to an aspect of an embodiment, a method may include obtaining data input including one or more words. The method may also include obtaining a set of emotions. The method may further include determining a set of expressed emotions and a set of expressed emotion probabilities based on the one or more words. Each expressed emotion of the set of expressed emotions may correspond to a different expressed emotion probability of the set of expressed emotion probabilities. Each expressed emotion of the set of expressed emotions may correspond with a different emotion of the set of emotions. The method may also include obtaining a set of likelihood probabilities. Each likelihood probability of the set of likelihood probabilities may correspond to a conditional probability of an expressed emotion of the set of expressed emotions given an experienced emotion of a group of experienced emotions. Each emotion of the group of experienced emotions may correspond with a different emotion of the set of emotions. The method may further include determining a set of experienced emotions of the group of experienced emotions and a set of experienced emotion probabilities based on the set of expressed emotion probabilities and the set of likelihood probabilities. Each experienced emotion of the set of experienced emotions may correspond to a different experienced emotion probability of the set of experienced emotion probabilities. The method may also include selecting an experienced emotion of the set of experienced emotions based on the selected experienced emotion corresponding to the highest experienced emotion probability of the set of experienced emotion probabilities. The method may further include presenting the selected experienced emotion in response to the selected experienced emotion being different from an expressed emotion of the set of expressed emotions corresponding to the highest expressed emotion probability of the set of expressed emotion probabilities.

The objects and advantages of the embodiments will be realized and achieved at least by the elements, features, and combinations particularly pointed out in the claims.

Both the foregoing general description and the following detailed description are given as examples and are explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

Figure 1:
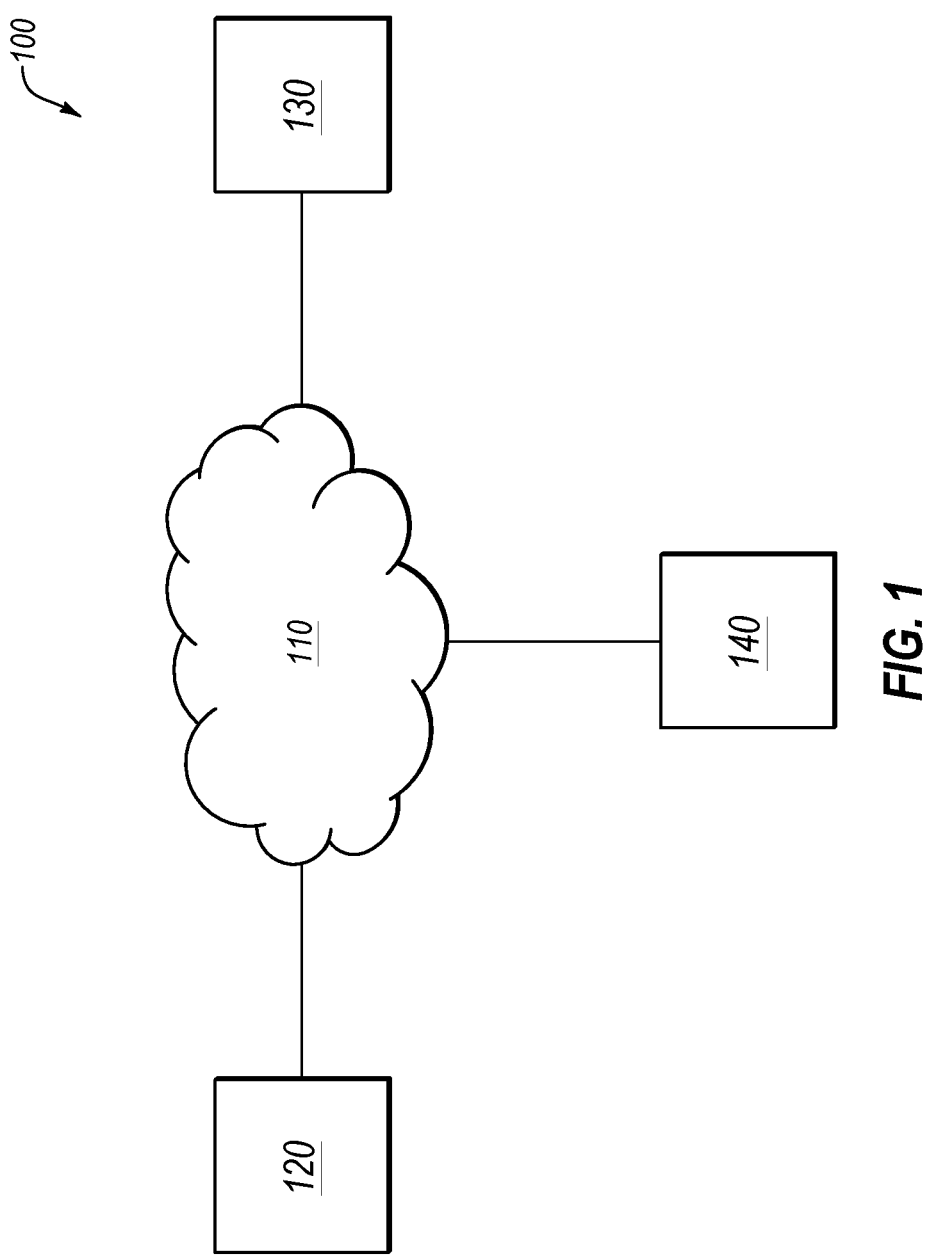
FIG. 1 is a diagram representing an example environment related to estimating experienced emotions.

Some embodiments described herein relate to methods and systems of the estimating experienced emotions. Currently, it may be difficult for human and/or artificial intelligence participants in a conversation with a human to determine the emotions being experienced by other participants in the conversation. For example, depending on the type of issue being discussed, human-to-human conversations may include varying amounts of emotional content. While some emotions may be expressed in the conversation, other emotions may be felt by the participants in the conversation or experienced internally by the participants.

Additionally, at times, an expressed emotion may not correspond with what emotions an individually is experiencing internally. For example, a person may express an emotion other than the emotion the person is experiencing because of socio-cultural norms. Because experienced emotions are within an individual, they may not be easily perceivable by others. It may be beneficial to understand both expressed and experienced emotions of individuals. Expressed and experienced emotions may potentially provide information about possible negative consequences in an individual. For example, an experienced feeling of extreme sadness may be expressed as anger. Understanding experienced emotions may also facilitate better communication between an end-user and a human in a conversational user interface. A knowledge of both expressed and experienced emotions may influence some cognitive processes of the end-user and may help the conversation be guided productively.

For example, an individual requesting emotional support, such as a user, may engage a conversational user interface. A human listener, such as a counselor, may participate in conversation with the individual. The individual and the human listener may "chat" or send messages electronically to each other. While some emotions may be expressed in the messages by the user, other emotions may be experienced internally by the user. An emotion may be expressed in a message when the emotion or a synonym of the emotion is expressed in the message. For example, "anger" may be expressed in the message when the user uses the word "angry," "mad," "furious," or other synonyms. For example, the user may say in a message "I am angry with my friend." Estimating experienced emotions of the present disclosure may allow a machine to analyze the messages and provide an assessment of the experienced emotions in the individual's messages to the human listener. For example, the user may be expressing "anger" externally by saying in a message "I am angry with my friend" but may be experiencing "fear" internally.

According to one or more embodiments described in the present disclosure, a text string of a user may be obtained. The text string may include one or more words. The user may be an individual requesting emotional support, an individual requesting customer support, an individual attempting to purchase a service or product, an employee, a manager, or any other person. A set of emotions may be obtained. The set of emotions may include foundational emotions that are common to many individuals. The emotions may include happiness, sadness, anger, fear, surprise, worry, and trouble. As the user interacts with a human listener, the text strings of the user may be analyzed to determine a set of expressed emotions that are expressed in the text strings of the user. The set of expressed emotions may be dynamic and may change as additional text strings of the user are obtained. For example, the first text strings may express anger while subsequent text strings may express fear. A set of likelihood probabilities may also be obtained. The set of likelihood probabilities may include the probability of an individual expressing a particular expressed emotion given that the individual is experiencing a particular experienced emotion. For example, the set of likelihood probabilities may include the probabilities of an individual expressing worry when the individual is experiencing happiness, sadness, anger, fear, surprise, worry, or trouble. A set of experienced emotions and experienced emotion probabilities may be determined based on the set of expressed emotions and the likelihood probabilities. The experienced emotion with the highest experienced emotion probabilities may be selected.

In some embodiments, the selected experienced emotion may be used to identify medication which may be beneficial to the user given the selected experienced emotion. The name of the identified medication may be provided to a pharmacy for fulfillment of a prescription or to a medical health professional for verification and writing of a prescription. Alternatively, the selected experienced emotion may be used to provide counseling to the user, to provide coaching to the user, to identify products the user may be interested in purchasing, to determine whether to hire the user, or for other purposes.

Embodiments of the present disclosure are explained with reference to the accompanying drawings.

FIG. 1 is a diagram representing an example environment 100 related to estimating experienced emotions. The environment 100 may include a network 110, a user device 120, a human listener device 130, and a medical professional device 140.

The network 110 may be configured to communicatively couple the user device 120, the human listener device 130, and the medical professional device 140. In some embodiments, the network 110 may include any network or configuration of networks configured to send and receive communications between systems and devices. In some embodiments, the network 110 may include a conventional type network, a wired or wireless network, and may have numerous different configurations. In some embodiments, the network 110 may also be coupled to or may include portions of a telecommunications network, including telephone lines such as a public switch telephone network (PSTN) line, for sending data in a variety of different communication protocols, such as a protocol used by a plain old telephone system (POTS).

The user device 120, the human listener device 130, and the medical professional device 140 may include any electronic or digital computing device. For example, each of the user device 120, the human listener device 130, and the medical professional device 140 may include a desktop computer, a laptop computer, a smartphone, a mobile phone, a tablet computer, a telephone, a phone console, or any other computing device. In some embodiments, the user device 120, the human listener device 130, and the medical professional device 140 may each include a computing system configured to perform operations described in this disclosure, among other operations. The computing systems may be similar to the computing system 600 described below with respect to FIG. 6.

In some embodiments, each of the user device 120, the human listener device 130, and the medical professional device 140 may be associated with different users. For example, in some embodiments, the user device 120 may be associated with a first individual. In these and other embodiments, the human listener device 130 may be associated with a second individual. In these and other embodiments, the medical professional device 140 may be associated with a third individual. In these and other embodiments, the first individual may be an individual communicating with others using, for example, a conversation user interface. For example, the first individual may be seeking help for emotional problems, may be researching products to purchase, or may be in a meeting with the first individual's work supervisor.

The second individual may be communicating with the first individual using the conversational user interface. For example, the second individual may be a counselor and may provide counseling to the first individual using the conversational user interface, may be a salesperson and may help the first individual determine which product to buy, or may be the supervisor of the first individual and may be conducting a review of the first individual's performance over the course of the year.

The third individual may be a medical professional associated with the first individual and/or the second individual. For example, the third individual may be a primary care physician of the first individual or a specialist physician of the first individual. Alternatively, the third individual may be a colleague of the second individual who is authorized to write prescriptions for prescription medications. Alternatively, the third individual may be a pharmacy which may be authorized to fulfill prescriptions. For example, a suggested prescription for the first individual may be sent from the user device 120 to the medical professional device 140 and/or from the human listener device 130 to the medical professional device 140. The third individual may authorize the fulfillment of the prescription, prescribe an alternative medication, or fulfill the prescription. Although depicted with three devices 120, 130, and 140, the environment 100 may include any number of devices. For example, in some embodiments, the environment 100 may include the user device 120 and the human listener device 130. Alternatively, the environment 100 may include the user device 120 and the medical professional device 140. Alternatively, the environment 100 may include the user device 120. Alternatively, the environment 100 may include the human listener device 130.

In some embodiments, a user may communicate with a human listener. In these and other embodiments, a device, such as the user device 120 or the human listener device 130 may obtain data input. For example, in some embodiments, the user and the human listener may be located in the same room, speaking with each other. The human listener device 130 may include a microphone which may record the words spoken by the user as data input including multiple words. Alternatively or additionally, in some embodiments, the user and the human listener may be located in different places. The user and the human listener may communicate with each other using the user device 120 and the human listener device 130, respectively. For example, the user may type a message into the user device 120, which may be sent to the human listener device 130 via the network 110. Alternatively, the user may speak into a microphone of the user device 120 and audio may be played back on a speaker of the human listener device 130.

A device, such as the human listener device 130, may obtain the data input, which may include multiple words. The human listener device 130 may also obtain a set of emotions. The set of emotions may include any number of emotions. For example, the set of emotions may include happiness, sadness, anger, fear, surprise, worry, and trouble. Alternatively or additionally, the set of emotions may include annoyed, anxious, bored, calm, confident, confused, disappointed, gratitude, guilt, nervous, pride, resentful, shame, vulnerable, or other emotions. In some embodiments, the set of emotions may include emotions of interest to the user, the human listener, and/or the medical professional.

The human listener device 130 may identify which emotions of the set of emotions are expressed in the data input. For example, the data input may include multiple words. Each word may be associated with one or more emotions. One word may be associated with multiple emotions and multiple words may each be associated with the same emotion. Based on the words in the data input, the human listener device 130 may determine at least one expressed emotion. Alternatively, the human listener device 130 may determine a set of expressed emotions and a set of expressed emotion probabilities. The set of expressed emotion probabilities may represent the probability that each emotion of the set of expressed emotions is being expressed in the data input.

In some embodiments, the human listener device 130 may obtain a set of emotion pairs. Each emotion pair of the set of emotion pairs may include an expressed emotion corresponding to the at least one expressed emotion, an experienced emotion, and a probability of the expressed emotion given the experienced emotion. In some embodiments, the human listener device 130 may obtain the set of emotion pairs from a database based on the expressed emotions determined in the data input. In some embodiments, the human database may be accessed via the network 110. Alternatively or additionally, in some embodiments, the database may be stored on a storage device of the human listener device 130. In these and other embodiments, the human listener device 130 may determine at least one experienced emotion based on the at least one expressed emotion and the set of emotion pairs.

Alternatively or additionally, in some embodiments, the human listener device 130 may obtain a set of likelihood probabilities. In some embodiments, the a device, such as the human listener device 130 or another device, may generate the set of likelihood probabilities by using a machine learning algorithm on an emotion data corpus, which may include multiple texts including emotion words. For example, in some embodiments, another device may generate the likelihood probabilities and the human listener device 130 may obtain the likelihood probabilities from the other device via the network 110. The set of likelihood probabilities may include relational information between expressed emotions and experienced emotions. The set of likelihood probabilities may include the conditional probability of expressing a particular emotion given that a user is experiencing a particular emotion. For example, a first likelihood probability in the set of likelihood probabilities may be the conditional probability of expressing happiness given that a user is experiencing sadness. A second likelihood probability may be the conditional probability of expressing happiness given that a user is experiencing happiness. In these and other embodiments, the human listener device 130 may determine a set of experienced emotions based on the set of expressed emotions and the set of likelihood probabilities.

In some embodiments, the human listener device 130 may present the experienced emotions on a display of the human listener device 130 such that the human listener, for example, a counselor, may see the experienced emotions to aid in providing counseling to the user. Alternatively or additionally, the human listener device 130 may access a database of medications associated with emotions, select a medication based on the experienced emotions, and send the name of the selected medication to the medical professional device 140.

Modifications, additions, or omissions may be made to the environment 100 without departing from the scope of the present disclosure. For example, in some embodiments, environment 100 may not include the network 110, the human listener device 130, or the medical professional device 140. In these and other embodiments, the user may enter text into the user device 120. An automated chat program on the user device 120 may respond to the text entered into the device based on identifying expressed emotions and predicting experienced emotions of the user. Alternatively or additionally, the user may speak into a microphone of the user device 120 and the automated chat program may respond to the words spoken based on identifying expressed emotions and predicting experienced emotions of the user.

Alternatively or additionally, in some embodiments, the environment 100 may not include the network 110, the user device 120, or the medical professional device 140. In these and other embodiments, a user may be speaking with a human listener. A microphone of the human listener device 130 may capture the words spoken by the user and a program on the human listener device 130 may identify expressed emotions and predicting experienced emotions of the user. The human listener device 130 may present the experienced emotions of the user on a display of the human listener device 130. The human listener may be able to suggest a course of treatment or to modify a conversation based on the experienced emotions.

Alternatively or additionally, in some embodiments, the human listener device 130 may access a database of medications associated with mental health. The human listener device 130 may select a medication from the database of medications based on the experienced emotions of the user. The human listener device 130 may notify the medical health professional associated with the user about the selected medication. The medical health professional may write a prescription for the selected medication for the user.

Alternatively or additionally, in some embodiments, the human listener may use the human listener device 130 to provide counseling to the user. For example, the human listener may obtain a diagnosis of a mental state of the user based on the experienced emotions of the user and the text strings or data input received from the user. The human listener may identify a treatment for the user based on the diagnosis and may provide the diagnosis to the user device 120.

Figure 2:
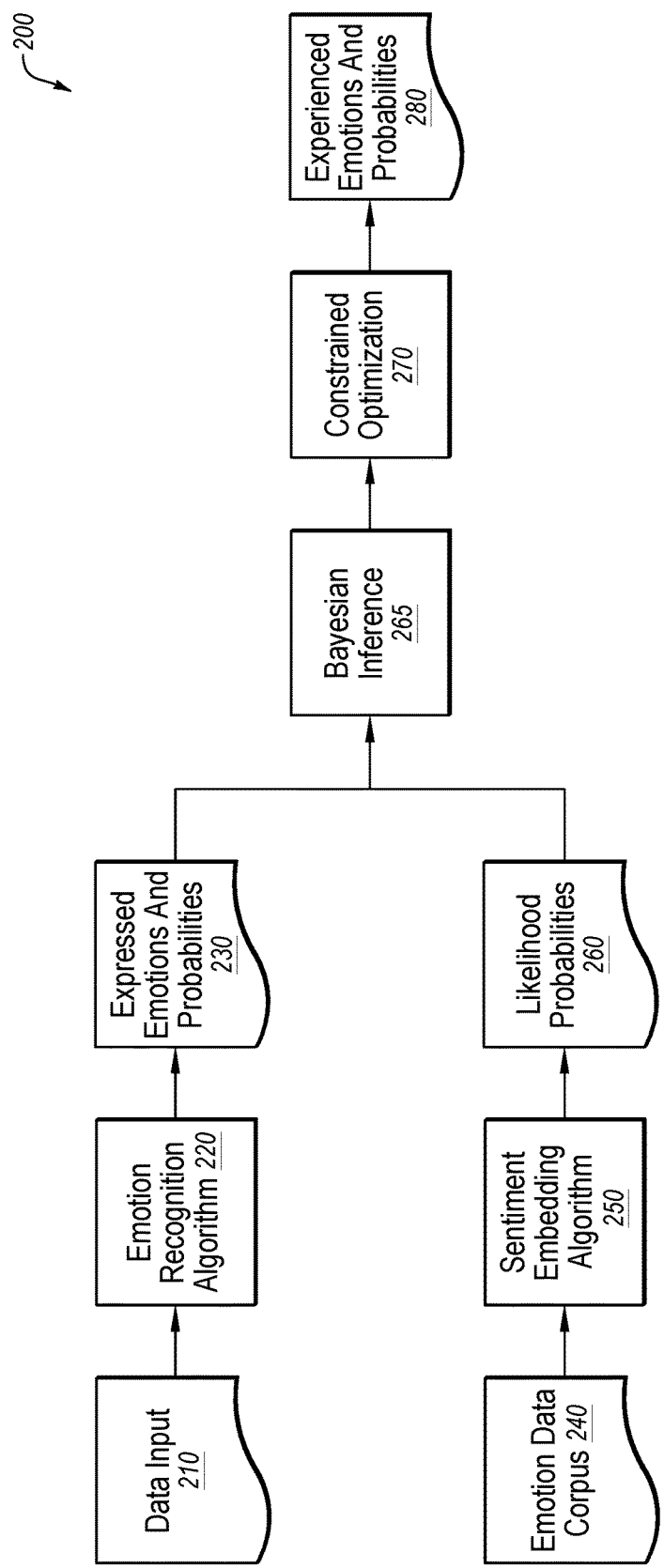
FIG. 2 is a diagram representing a process of estimating experienced emotions.

FIG. 2 is a diagram representing a process 200 of estimating experienced emotions. In some embodiments, the process 200 may be performed by one or more devices, such as the user device 120, the human listener device 130, or the medical professional device 140. Alternatively or additionally, in some embodiments, parts of the process 200 may be performed by other devices. The process 200 may include an emotion recognition algorithm 220, a sentiment embedding algorithm 250, and a constrained optimization algorithm 270. The process 200 may transform data input 210 and an emotion data corpus 240 into experienced emotions and probabilities 280.

The data input 210 may include one or more words. For example, in some embodiments, the data input 210 may include textual input such as electronic messages including text messages, instant messages, social media messages, emails, or other messages. Alternatively or additionally, the data input 210 may include audio input such as audio associated with one or more people speaking. Alternatively or additionally, the data input 210 may include video input such as a video associated with one or more people performing sign language. The data input 210 may include any number of words from any number of sources. For example, in some embodiments, the data input may include multiple participants in a conversation and may include 1 word, 50 words, 1000 words, or any number of words.

The emotion recognition algorithm 220 may compare the words of the data input 210 with an emotion vocabulary. The emotion vocabulary may include a set of emotions and a set of words related to each emotion of the set of emotions. For example, if the set of emotions includes a first emotion, a second emotion, and a third emotion, the emotion vocabulary may include the first emotion and a set of words related to the first emotion, the second emotion and a set of words related to the second emotion, and the third emotion and a set of words related to the third emotion. In some embodiment, the set of words related to each emotion may include a set of synonyms for each emotion.

The emotion recognition algorithm 220 may compare the words of the data input 210 with each set of words related to each emotion of the emotion vocabulary. Based on the comparison, the emotion recognition algorithm 220 may determine an expressed emotion probability, $P_{i,expressed}$, for each emotion of the emotion vocabulary. The expressed emotion probability for each emotion may represent a probability that the emotion is expressed in the data input 210. For example, in some embodiments, the words in the data input 210 may be matched for co-occurrence with sets of words in the emotion vocabulary. The matches may be weighted or normalized based on a frequency of occurrence to obtain an experienced emotion probability for each emotion. Alternatively or additionally, a different algorithm may be employed to determine the expressed emotions and the expressed emotion probabilities 230. In some embodiments, the emotion recognition algorithm 220 may output the expressed emotions and the expressed emotion probabilities 230.

The expressed emotions and probabilities 230 may include the emotions and probabilities identified by the emotion recognition algorithm 220. In some embodiments, the expressed emotions with the highest expressed emotion probabilities may be identified as the expressed emotions.

The emotion data corpus 240 may include multiple texts that reflect emotions. In some embodiments, the emotion data corpus 240 may include thousands of texts, each text including multiple words. In some embodiments, the emotion data corpus 240 may include texts from multiple people and may not be limited to texts from a user associated with the data input 210.

The sentiment embedding algorithm 250 may determine sentiment embeddings associated with different emotions based on the emotion data corpus 240. Because the emotion data corpus 240 may include texts from multiple users, the sentiment embeddings may be reflective of a general relatedness between two emotion-indicating words and may not be reflective of a particular relatedness between two words for a user associated with the data input.

In some embodiments, sentiment embeddings may be sentiment-specific word embeddings. Traditional context-based word embeddings may model the contexts of words but may ignore the sentiment information associated with the words. Thus words with opposite meaning but that are used in similar contexts, such as good and bad, may be mapped close to each other due to having similar traditional context-based word embeddings. In contrast, sentiment embeddings include the sentiment of words. By including both context and sentiment, a machine learning algorithm, such as a neural network algorithm, may determine the sentiment embeddings of different words in a continuous spectrum, such that words that are semantically similar but that have different sentiment, such as happiness and sadness, are have dissimilar sentiment embeddings.

In some embodiments, the sentiment embedding algorithm 250 may determine the likelihood probabilities 260 by determining a similarity between the sentiment embeddings associated with each emotion. For example, if there are three emotions, happiness, sadness, and anger, there may be six similarities between the sentiment embeddings: happiness-happiness, happiness-sadness, happiness-anger, sadness-sadness, sadness-anger, and anger-anger. In some embodiments, the similarity may be order irrelevant such that the happiness-sadness similarity is equivalent to the sadness-happiness similarity. In some embodiments, the similarity may be determined based on a distance between the sentiment embeddings of emotions.

The similarity between two emotions, i and j may be represented as $r_{i,j}$. As discussed above, in some embodiments, $r_{i,j}$ may be equal to $r_{j,i}$. The likelihood probability of a particular expressed emotion, for example emotion i, given a particular experienced emotion, for example emotion j, may be determined as:

$$P_l(i \mid j) = \frac{r_{i,j}}{\sum_k r_{i,k}},$$

where $P_l(i|j)$ represents the likelihood probability of expressing emotion i given that emotion j is experienced and $\Sigma_k r_{i,k}$ represents the sum of the similarities $r_{i,k}$ between emotion i and each emotion k. Continuing the above example, for the three emotions, happiness, sadness, and anger, there may be nine likelihood probabilities between the emotions: happiness-happiness, happiness-sadness, happiness-anger, sadness-happiness, sadness-sadness, sadness-anger, anger-happiness, anger-sadness, and anger-anger. In some embodiments, the likelihood probability may be order relevant such that the likelihood probability of expressing happiness given that sadness is being experienced is not equivalent to the likelihood probability of expressing sadness given that happiness is being experienced. Thus, while the similarities may be symmetric such that for each i and j, $r_{i,j}=r_{j,i}$, the likelihood probabilities may not be symmetric such that in general $P_l(i|j) \neq P_l(j|i)$, $i \neq j$.

In some embodiments, the likelihood probabilities may be determined based on the emotion data corpus 240 which may not be specific to a particular user associated with the data input 210. However, the emotion data corpus 240 and the resulting likelihood probabilities 260 may be representative of average likelihood probabilities across the population associated with the emotion data corpus 240.

The expressed emotions and probabilities 230 may be combined with the likelihood probabilities 260 using Bayesian Inference 265. Using Bayes rule of total probability, each expressed emotion may be written as a function of likelihood probabilities and experienced emotion probabilities. Thus, using Bayes rule of total probability, the probability that a particular emotion, for example i, is expressed may be determined as: $P_{i,expressed} = \Sigma_j P_l(i|j) P_{j,experienced}$ where j represents each experienced emotion and $P_{j,experienced}$ represents the probability that emotion j is experienced. If there are m expressed emotions i and n experienced emotions j, where n>m, there may be m equations $P_{i,expressed} = \Sigma_j P_l(i|j) P_{j,experienced}$ (each $P_{i,expressed}$) with n variables (each $P_{j,experienced}$). The experienced emotion probabilities $P_{j,experienced}$ may be denoted as an n dimensional column $$\text{vector } x = \begin{bmatrix} P_{1,experienced} \\ \vdots \\ P_{n,experienced} \end{bmatrix}.$$

The likelihood probabilities $P_l(i|j)$ may be denoted as an m×n $$\text{matrix } L = \begin{bmatrix} P_l(1|1) & \cdots & P_l(1|n) \\ \vdots & \ddots & \vdots \\ P_l(m|1) & \cdots & P_l(m|n) \end{bmatrix}.$$

The expressed emotions $P_{i,expressed}$ may be denoted as an m dimensional column $$\text{vector } t = \begin{bmatrix} P_{1,expressed} \\ \vdots \\ P_{m,expressed} \end{bmatrix}.$$

In some embodiments, the m equations with n variables generated using Bayesian Inference 265 may be solved using constrained optimization 270 to generate the experienced emotions and probabilities 280. The m equations with n variables may be solved as $\min \|Lx-t\|_2^2$. This may represent the minimum of the square of the Euclidean norm of Lx−t. Because the sum of the experienced emotion probabilities is equal to 1 and each experienced emotion probability is nonnegative, $\min \|Lx-t\|_2^2$ is a minimum norm optimization problem with the constraints that $\|x\|_1 = 1$ and that each $x_j = P_{j,experienced} \geq 0$. In some embodiments, this may be solved as a constrained optimization problem.

The constrained optimization problem $\min \|Lx-t\|_2^2$, $\|x\|_1 = 1$ and $x_j = P_{j,experienced} \geq 0$, may be solved by applying Karush-Kuhn-Tucker conditions. For example, the condition may be: $D\|Lx-t\|_2^2 + \lambda \times D(x^T 1_n - 1) + \mu x = 0$, where D represents the derivative, $1_n$ is an n dimensional column vector of 1, A is the Lagrange multiplier, and $\mu = [\mu_1 \mu_2 \ldots \mu_n]$ is a Karush-Kuhn-Tucker multiplier such that $\mu x = 0$ and each $\mu_i < 0$. Solving the constrained optimization problem may result in a set of estimated experienced emotion probabilities, $P_{j,experienced}$. The constrained optimization 270 may output the experienced emotions and probabilities 280. In some embodiments, the experienced emotions corresponding with the highest experienced emotion probabilities may be selected as the experienced emotions.

Modifications, additions, or omissions may be made to the process 200 without departing from the scope of the present disclosure. For example, in some embodiments, one or more steps of the process 200, such as, for example, the sentiment embedding algorithm, may be performed by other processes.

Figure 3:
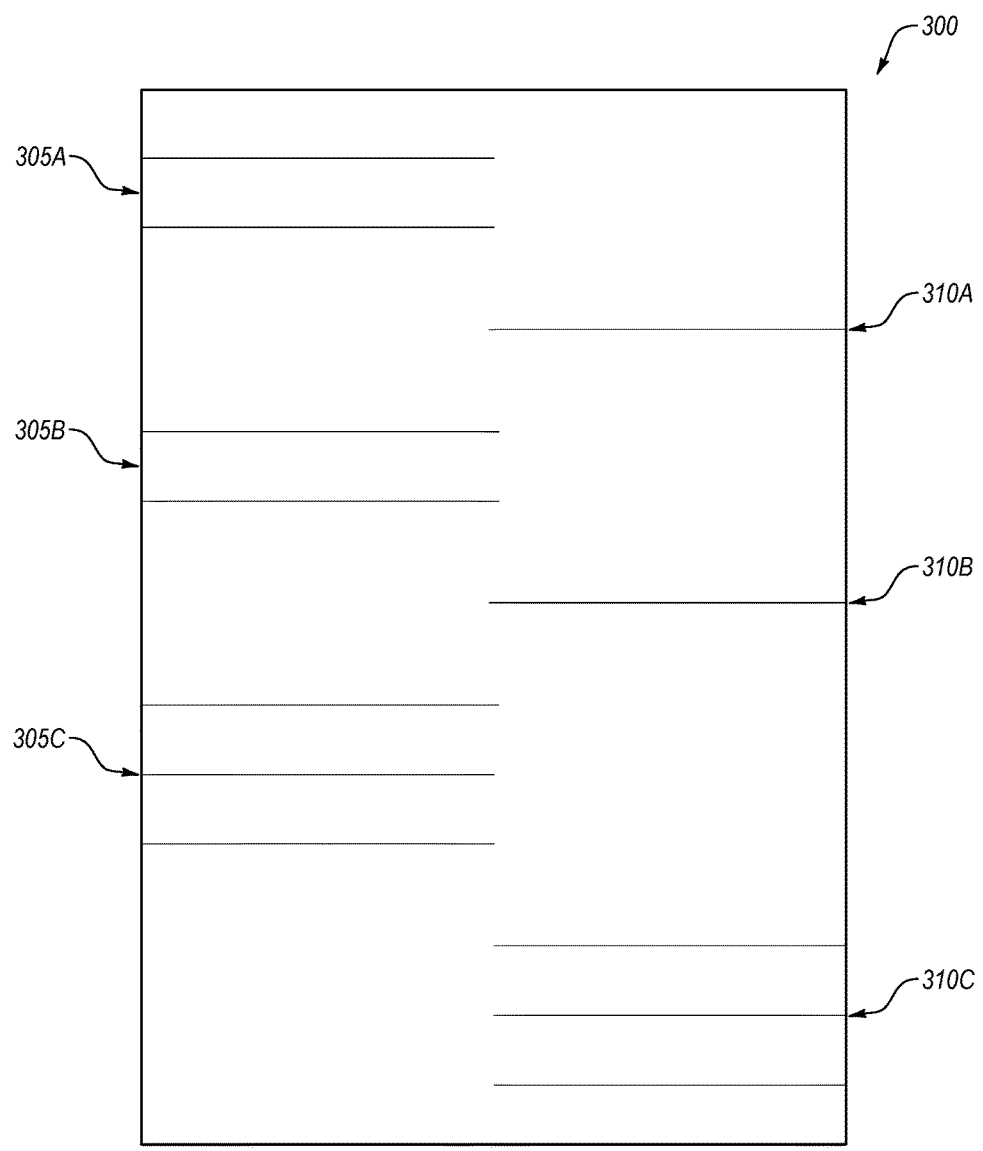
FIG. 3 illustrates an example conversational user interface.

FIG. 3 illustrates an example conversational user interface 300. The conversational user interface 300 may include a display with a first user text string 305A, a second user text string 305B, a third user text string 305C (collectively the user text strings 305), a first human listener response string 310A, a second human listener response string 310B, and a third human listener response string 310C (collectively the human listener response strings 310).

The user text strings 305 and the human listener response strings 310 may be presented in chronological order in the conversational user interface 300 beginning from the top of the conversational user interface 300. For example, the second user text string 305B may be displayed on the conversational user interface 300 after the first human listener response string 310A and before the second human listener response string 310B. Although the user text strings 305 and the human listener response strings 310 are depicted as lines, in practice the user text strings 305 and the human listener response strings 310 may represent words and/or letters entered by a user and/or by a human listener, respectively.

As the user enters text into the conversational user interface 300, expressed and experienced emotions may be determined based on the user text strings 305. For example, after entering the first user text string 305A, one or more expressed and experienced emotions may be determined based on the first user text string 305A. The determined expressed and/or experienced emotions may be presented to the human listener but may not be presented to the user. In response to obtaining the expressed and/or experienced emotions, the human listener may send the first human listener response string 310A to the user.

As the user continues to enter the second user text string 305B and the third user text string 305C, the expressed and/or experienced emotions may be updated based on the first user text string 305A, the second user text string 305B, and/or the third user text string 305C. For example, in some embodiments, after the user enters the second user text string 305B, the expressed and experienced emotions may be updated based on both the first user text string 305A and the second user text string 305B. Alternatively, in some embodiments, after the user enters the second user text string 305B, the expressed and experienced emotions may be updated based on the second user text string 305B.

Similarly, in some embodiments, after the user enters the third user text string 305C, the expressed and experienced emotions may be updated based on the first user text string 305A, the second user text string 305B, and the third user text string 305C. Alternatively, in some embodiments, after the user enters the third user text string 305C, the expressed and experienced emotions may be updated based on the second user text string 305B and the third user text string 305C. Alternatively, in some embodiments, after the user enters the third user text string 305C, the expressed and experienced emotions may be updated based on the third user text string 305C.

In some embodiments, the expressed and experienced emotions may be updated based on every user text string 305. Alternatively, in some embodiments, the expressed and experienced emotions may be updated based on a specific number of user text strings 305, such as, for example, the two most recent user text strings 305. Alternatively or additionally, in some embodiments, the expressed and experienced emotions may be updated based on a specific number of words in the user text strings 305, such as, for example, the most recent one hundred words. Alternatively or additionally, in some embodiments, the expressed and experienced emotions may be updated based on user text strings 305 from the most recent period of time. For example, the expressed and experienced emotions may be updated based on the user text strings 305 from the most recent hour, ten minutes, five minutes, or any other duration of time.

Modifications, additions, or omissions may be made to the conversational user interface 300 without departing from the scope of the present disclosure. For example, in some embodiments, the user text strings 305 and/or the human listener response strings 310 may include data files such as, for example, audio files and/or video files. For example, the first human listener response string 310A may include an icon of a speaker. The user may select the icon of the speaker to listen to audio of the first human listener response string 310A.

Figure 4A:
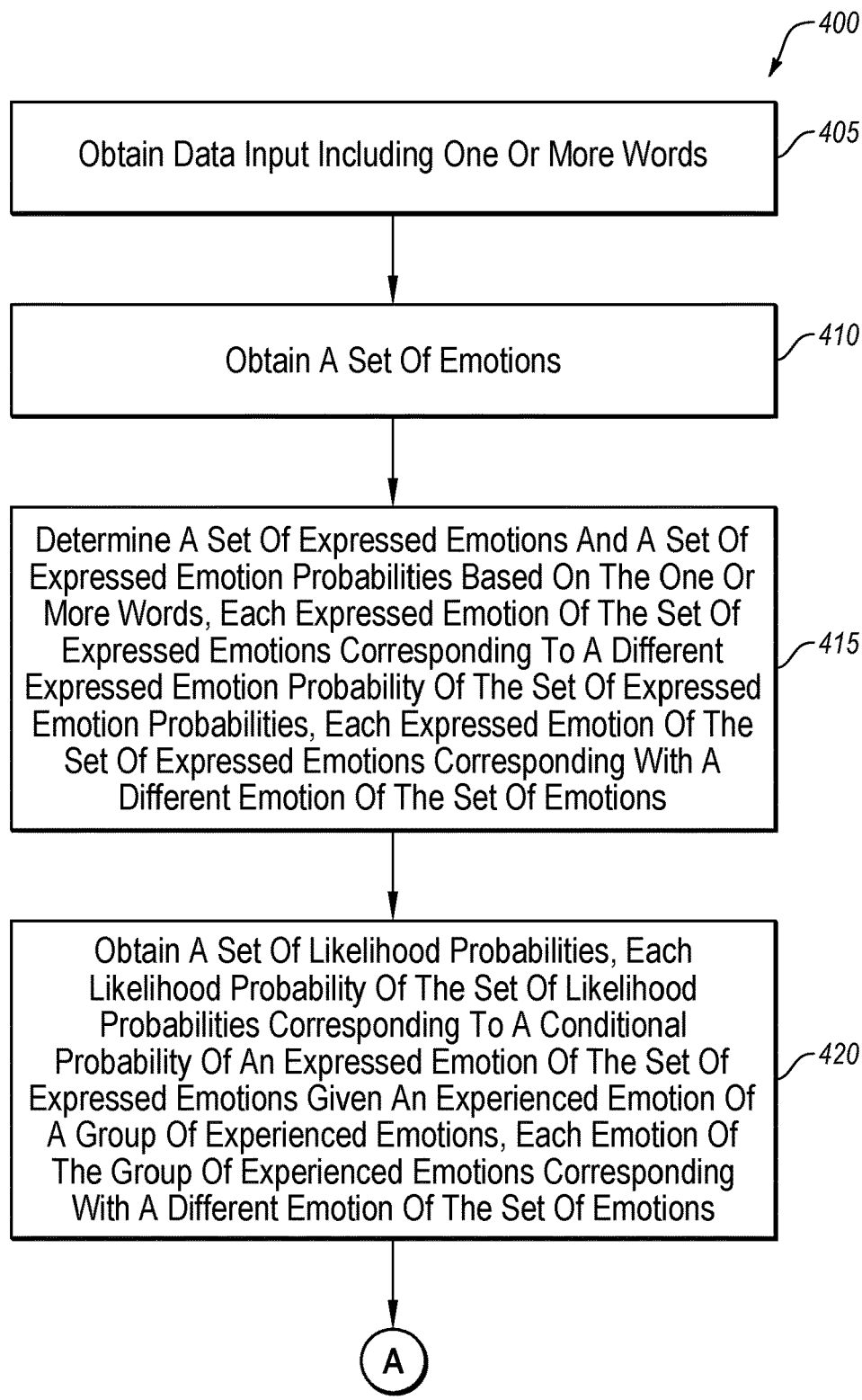
FIGS. 4A and 4B depict a flowchart of an example method of estimating experienced emotions.
Figure 4B:
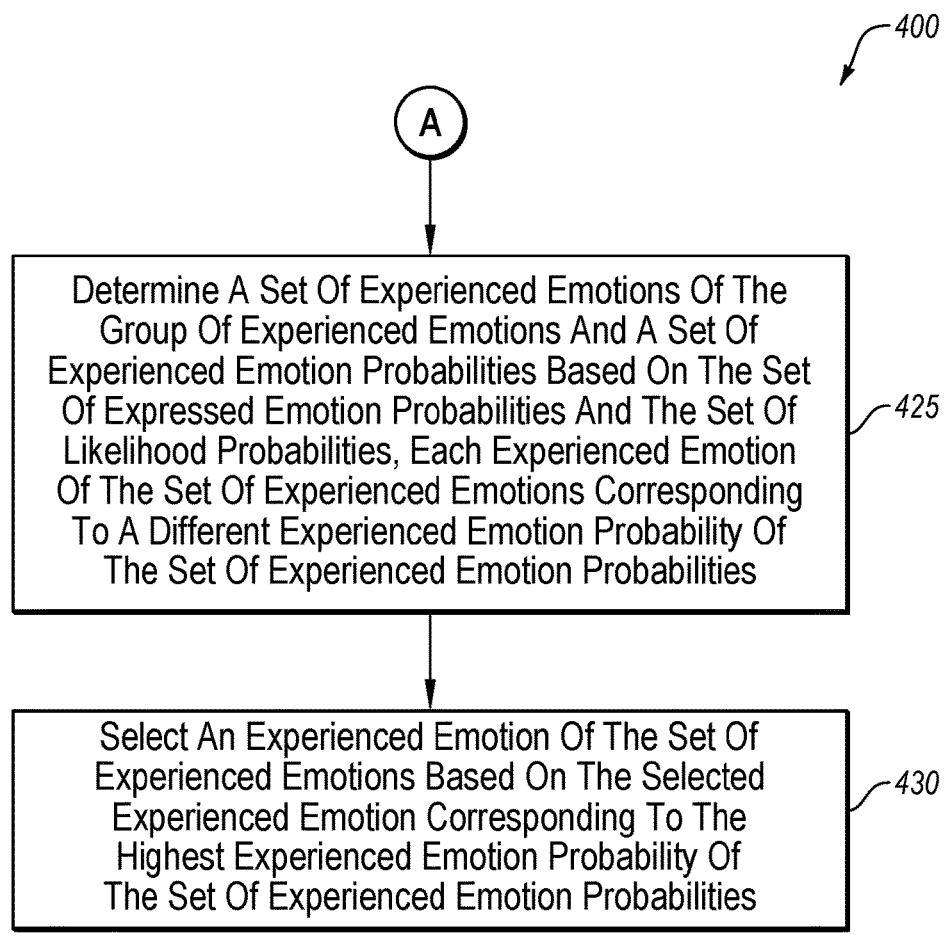

FIGS. 4A and 4B are a flowchart of an example method 400 of estimating experienced emotions. The method 400 may be arranged in accordance with at least one embodiment described in the present disclosure. The method 400 may be performed, in whole or in part, in some embodiments by a system and/or environment, such as the environment 100 and/or the system 600 of FIGS. 1 and 6, respectively. In these and other embodiments, the method 400 may be performed based on the execution of instructions stored on one or more non-transitory computer-readable media. Although illustrated as discrete blocks, various blocks may be divided into additional blocks, combined into fewer blocks, or eliminated, depending on the desired implementation.

The method 400 may begin at block 405, where data input including one or more words may be obtained. In some embodiments, the data input may include a text string. In block 410, a set of emotions may be obtained. In some embodiments, the set of emotions may include one or more of happiness, sadness, anger, fear, surprise, worry, and trouble.

In block 415, a set of expressed emotions and a set of expressed emotion probabilities may be determined based on the one or more words. Each expressed emotion of the set of expressed emotions may correspond to a different expressed emotion probability of the set of expressed emotion probabilities. Each expressed emotion of the set of expressed emotions may correspond with a different emotion of the set of emotions. In some embodiments, determining the set of expressed emotions and the set of expressed emotion probabilities may include obtaining an emotion vocabulary including multiple emotion words related to each emotion of the set of emotions, comparing the one or more words of the data input with the multiple emotion words, identifying an expressed emotion probability for each emotion of the set of emotions based on the comparing, identifying emotions of the set of emotions associated with an identified expressed emotion probability greater than zero as the set of expressed emotions, and identifying identified expressed emotion probabilities greater than zero as the set of expressed emotion probabilities.

In block 420, a set of likelihood probabilities may be obtained. Each likelihood probability of the set of likelihood probabilities may correspond to a conditional probability of an expressed emotion of the set of expressed emotions given an experienced emotion of a group of experienced emotions. Each emotion of the group of experienced emotions may correspond with a different emotion of the set of emotions. In some embodiments, obtaining the set of likelihood probabilities may include obtaining sentiment embeddings associated with each emotion of the set of expressed emotions and the group of experienced emotions, obtaining a similarity between each pair of emotions of the set of expressed emotions and the group of experienced emotions based on the sentiment embeddings, and normalizing the similarities between each pair of emotions to generate a conditional probability of an expressed emotion given an experienced emotion.

In block 425, a set of experienced emotions of the group of experienced emotions and a set of experienced emotion probabilities may be determined based on the set of expressed emotion probabilities and the set of likelihood probabilities. Each experienced emotion of the set of experienced emotions may correspond to a different experienced emotion probability of the set of experienced emotion probabilities. In some embodiments, determining the set of experienced emotions and a set of experienced emotion probabilities may include, for each expressed emotion of the set of expressed emotions, generating an equation equating the expressed emotion probability associated with the expressed emotion to a sum of products of the conditional probability of the expressed emotion given each experienced emotion with the probability of the expressed emotion and solving the generated equations to determine the set of experienced emotions and the set of experienced emotion probabilities. In some embodiments, solving the generated equations may include solving the generated equations using constrained optimization subject to a constraint of the sum of the set of experienced emotion probabilities equaling 1 and a constraint of each probability of the set of experienced emotion probabilities being non-negative.

In block 430, an experienced emotion of the set of experienced emotions may be selected based on the selected experienced emotion corresponding to the highest experienced emotion probability of the set of experienced emotion probabilities.

One skilled in the art will appreciate that, for this and other processes, operations, and methods disclosed herein, the functions and/or operations performed may be implemented in differing order. Furthermore, the outlined functions and operations are only provided as examples, and some of the functions and operations may be optional, combined into fewer functions and operations, or expanded into additional functions and operations without detracting from the essence of the disclosed embodiments.

For example, in some embodiments, the method 400 may further include accessing a database of medications associated with mental health. In these and other embodiments, the method 400 may further include selecting a medication from the database of medications based on the selected experienced emotion in response to the selected experienced emotion being different from an expressed emotion of the set of expressed emotions corresponding to the highest expressed emotion probability of the set of expressed emotion probabilities. In these and other embodiments, the method 400 may further include notifying a medical health professional associated with a user associated with the data input about the selected medication.

Alternatively or additionally, in some embodiments, the method 400 may further include providing counseling to the user. In these and other embodiments, the method 400 may further include obtaining a diagnosis of a mental state of the user based on the selected experienced emotion and based on the data input. Providing counseling to the user may include identifying a treatment for the user based on the diagnosis. Alternatively or additionally, in some embodiments, the method 400 may further include presenting the selected experienced emotion.

Figure 5:
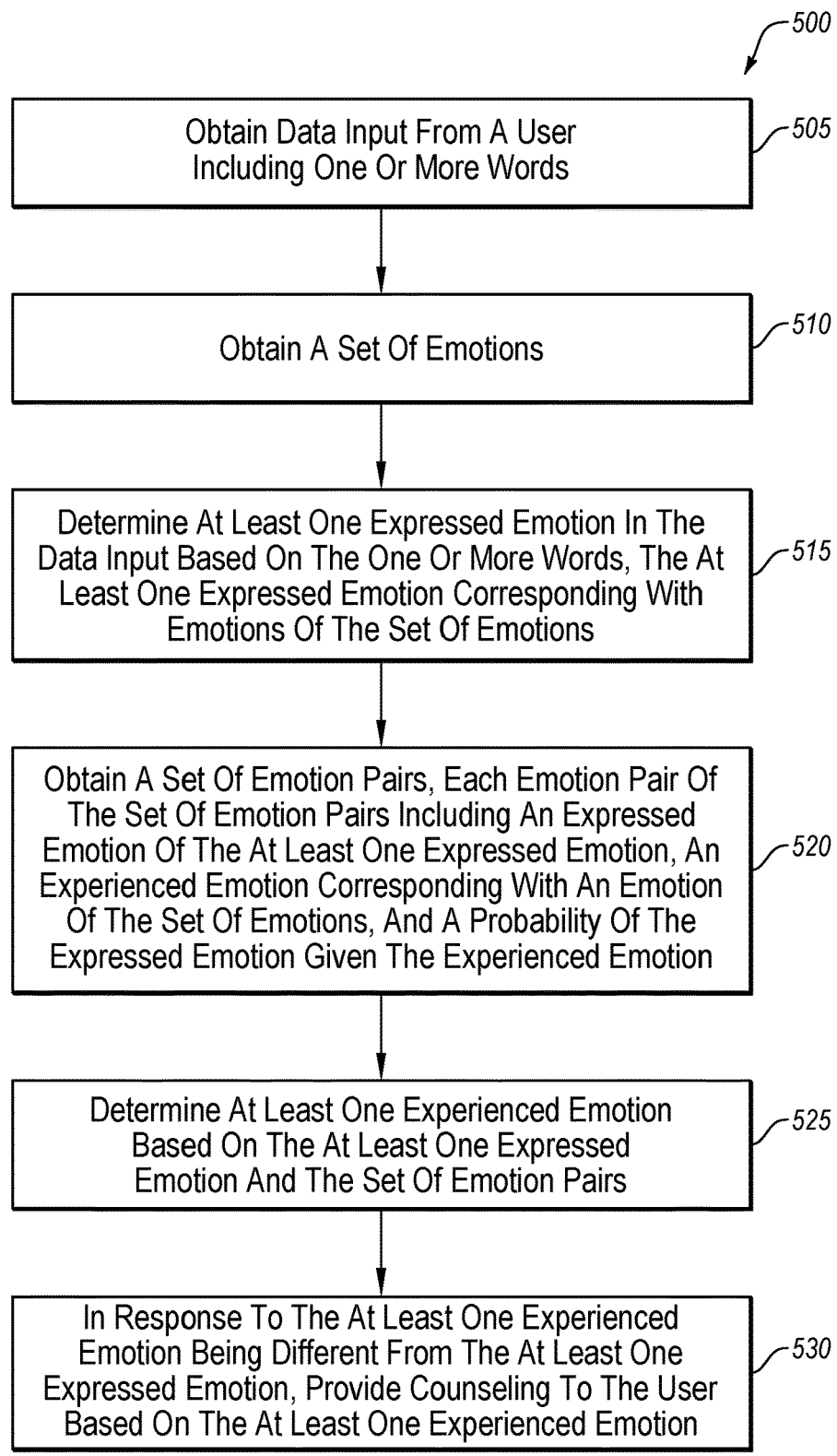
FIG. 5 depicts a flowchart of another example method of estimating experienced emotions.

FIG. 5 is a flowchart of another example method 500 of estimating experienced emotions. The method 500 may be arranged in accordance with at least one embodiment described in the present disclosure. The method 500 may be performed, in whole or in part, in some embodiments by a system and/or environment, such as the environment 100 and/or the system 600 of FIGS. 1 and 6, respectively. In these and other embodiments, the method 500 may be performed based on the execution of instructions stored on one or more non-transitory computer-readable media. Although illustrated as discrete blocks, various blocks may be divided into additional blocks, combined into fewer blocks, or eliminated, depending on the desired implementation.

The method 500 may begin at block 505, data input including one or more words may be obtained from a user. In block 510, a set of emotions may be obtained. In some embodiments, the set of emotions may include one or more of happiness, sadness, anger, fear, surprise, worry, and trouble.

In block 515, at least one expressed emotion may be determined in the data input based on the one or more words. The at least one expressed emotion may correspond with emotions of the set of emotions. In some embodiments, determining the at least one expressed emotion may include obtaining an emotion vocabulary including multiple emotion words related to each emotion of the set of emotions, comparing the one or more words of the data input with the multiple emotion words, identifying an expressed emotion probability for each emotion of the set of emotions based on the comparing, and identifying emotions of the set of emotions associated with an identified expressed emotion probability greater than zero as the at least one expressed emotion.

In block 520, a set of emotion pairs may be obtained. Each emotion pair of the set of emotion pairs may include an expressed emotion of the at least one expressed emotion, an experienced emotion corresponding with an emotion of the set of emotions, and a probability of the expressed emotion given the experienced emotion. In block 525, at least one experienced emotion may be determined based on the at least one expressed emotion and the set of emotion pairs. In block 530, counseling may be provided to the user based on the at least one experienced emotion in response to the at least one experienced emotion being different from the at least one expressed emotion.

One skilled in the art will appreciate that, for this and other processes, operations, and methods disclosed herein, the functions and/or operations performed may be implemented in differing order. Furthermore, the outlined functions and operations are only provided as examples, and some of the functions and operations may be optional, combined into fewer functions and operations, or expanded into additional functions and operations without detracting from the essence of the disclosed embodiments.

For example, in some embodiments, the method 500 may further include obtaining a diagnosis of a mental state of the user based on the at least one experienced emotion and based on the data input. In these and other embodiments, providing counseling to the user may include identifying a treatment for the user based on the diagnosis.

Figure 6:
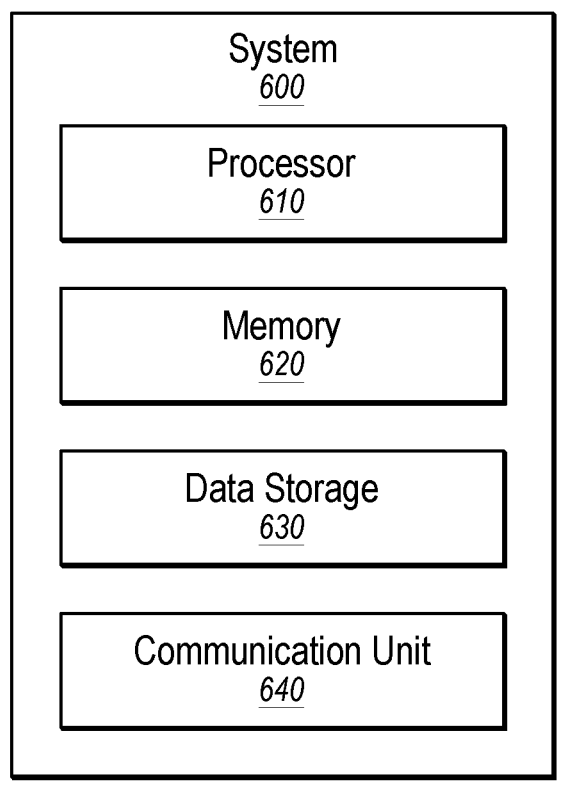
FIG. 6 illustrates an example computing system that may be configured for estimating experienced emotions.

FIG. 6 illustrates an example system 600, according to at least one embodiment described herein. The system 600 may include any suitable system, apparatus, or device configured to identify and extract information. The system 600 may include a processor 610, a memory 620, a data storage 630, and a communication unit 640, which all may be communicatively coupled. The data storage 630 may include various types of data, such as search paths and ratings of source materials.

Generally, the processor 610 may include any suitable special-purpose or general-purpose computer, computing entity, or processing device including various computer hardware or software modules and may be configured to execute instructions stored on any applicable computer-readable storage media. For example, the processor 610 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data.

Although illustrated as a single processor in FIG. 6, the processor 610 may include any number of processors distributed across any number of network or physical locations that are configured to perform individually or collectively any number of operations described herein. In some embodiments, the processor 610 may interpret and/or execute program instructions and/or process data stored in the memory 620, the data storage 630, or the memory 620 and the data storage 630. In some embodiments, the processor 610 may fetch program instructions from the data storage 630 and load the program instructions into the memory 620.

After the program instructions are loaded into the memory 620, the processor 610 may execute the program instructions, such as instructions to perform the methods 400 and/or 500 of FIGS. 4 and 5, respectively. The processor 610 may fetch the corresponding program instructions and may load the program instructions in the memory 620. After the program instructions are loaded into the memory 620, the processor 610 may execute the program instructions such that the computing system may implement the operations associated with the above-recited components as directed by the instructions.

The memory 620 and the data storage 630 may include computer-readable storage media or one or more computer-readable storage mediums for carrying or having computer-executable instructions or data structures stored thereon. Such computer-readable storage media may be any available media that may be accessed by a general-purpose or special-purpose computer, such as the processor 610.

By way of example, and not limitation, such computer-readable storage media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 610 to perform a certain operation or group of operations.

The communication unit 640 may include any component, device, system, or combination thereof that is configured to transmit or receive information over a network. In some embodiments, the communication unit 640 may communicate with other devices at other locations, the same location, or even other components within the same system. For example, the communication unit 640 may include a modem, a network card (wireless or wired), an infrared communication device, a wireless communication device (such as an antenna), and/or chipset (such as a Bluetooth device, an 802.6 device (e.g., Metropolitan Area Network (MAN)), a WiFi device, a WiMax device, cellular communication facilities, and/or others), and/or the like. The communication unit 640 may permit data to be exchanged with a network and/or any other devices or systems described in the present disclosure. For example, the communication unit 640 may allow the system 600 to communicate with other systems, such as the user device 120, the human listener device 130, and the medical professional device 140 of FIG. 1.

Modifications, additions, or omissions may be made to the system 600 without departing from the scope of the present disclosure. For example, the data storage 630 may be multiple different storage mediums located in multiple locations and accessed by the processor 610 through a network.

As indicated above, the embodiments described herein may include the use of a special purpose or general purpose computer (e.g., the processor 610 of FIG. 6) including various computer hardware or software modules, as discussed in greater detail below. Further, as indicated above, embodiments described herein may be implemented using computer-readable media (e.g., the memory 620 or data storage 630 of FIG. 6) for carrying or having computer-executable instructions or data structures stored thereon.

As used herein, the terms "module" or "component" may refer to specific hardware implementations configured to perform the actions of the module or component and/or software objects or software routines that may be stored on and/or executed by general purpose hardware (e.g., computer-readable media, processing devices, and/or others) of the computing system. In some embodiments, the different components, modules, engines, and services described herein may be implemented as objects or processes that execute on the computing system (e.g., as separate threads). While some of the systems and methods described herein are generally described as being implemented in software (stored on and/or executed by general purpose hardware), specific hardware implementations or a combination of software and specific hardware implementations are also possible and contemplated. In this description, a "computing entity" may be any computing system as previously defined herein, or any module or combination of modulates running on a computing system.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," and/or others).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, and/or others Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

What is claimed is:

1. A method for estimating experienced emotions of a user, comprising:

obtaining a text string of a user, the text string including one or more words;

obtaining a set of emotions;

determining a set of expressed emotions and a set of expressed emotion probabilities based on the one or more words, each expressed emotion of the set of expressed emotions corresponding to a different expressed emotion probability of the set of expressed emotion probabilities, each expressed emotion of the set of expressed emotions corresponding with a different emotion of the set of emotions;

obtaining a set of likelihood probabilities, each likelihood probability of the set of likelihood probabilities corresponding to a conditional probability of an expressed emotion of the set of expressed emotions given an experienced emotion of a group of experienced emotions, each experienced emotion of the group of experienced emotions corresponding with a different emotion of the set of emotions;

determining a set of experienced emotions of the group of experienced emotions and a set of experienced emotion probabilities based on the set of expressed emotion probabilities and the set of likelihood probabilities, each experienced emotion of the set of experienced emotions corresponding to a different experienced emotion probability of the set of experienced emotion probabilities;

selecting an experienced emotion of the set of experienced emotions based on the selected experienced emotion corresponding to the highest experienced emotion probability of the set of experienced emotion probabilities;

accessing a database of medications associated with mental health;

in response to the selected experienced emotion being different from an expressed emotion of the set of expressed emotions corresponding to the highest expressed emotion probability of the set of expressed emotion probabilities, selecting a medication from the database of medications based on the selected experienced emotion; and notifying a medical health professional associated with the user about the selected medication.

2. The method of claim 1, wherein determining the set of expressed emotions and the set of expressed emotion probabilities comprises:

obtaining an emotion vocabulary including a plurality of emotion words related to each emotion of the set of emotions;

comparing the one or more words of the text string with the plurality of emotion words;

based on the comparing, identifying an expressed emotion probability for each emotion of the set of emotions;

identifying emotions of the set of emotions associated with an identified expressed emotion probability greater than zero as the set of expressed emotions; and identifying identified expressed emotion probabilities greater than zero as the set of expressed emotion probabilities.

3. The method of claim 1, wherein obtaining the set of likelihood probabilities comprises:

obtaining sentiment embeddings associated with each emotion of the set of expressed emotions and the group of experienced emotions;

obtaining a similarity between each pair of emotions of the set of expressed emotions and the group of experienced emotions based on the sentiment embeddings; and normalizing the similarity between each pair of emotions to generate a conditional probability of an expressed emotion given an experienced emotion.

4. The method of claim 3, wherein determining the set of experienced emotions and the set of experienced emotion probabilities comprises:

for each expressed emotion of the set of expressed emotions, generating an equation equating the expressed emotion probability associated with the expressed emotion to a sum of products of the conditional probability of the expressed emotion given each experienced emotion with the probability of the expressed emotion; and solving the generated equations to determine the set of experienced emotions and the set of experienced emotion probabilities.

5. The method of claim 4, wherein solving the generated equations includes solving the generated equations using constrained optimization subject to a constraint of the sum of the set of experienced emotion probabilities equaling 1 and a constraint of each probability of the set of experienced emotion probabilities being non-negative.

6. The method of claim 1, further comprising providing counseling to the user.

7. The method of claim 6, further comprising obtaining a diagnosis of a mental state of the user based on the selected experienced emotion and based on the text string and wherein providing counseling to the user comprises identifying a treatment for the user based on the diagnosis.

8. The method of claim 1, wherein the set of emotions includes one or more of: happiness, sadness, anger, fear, surprise, worry, and trouble.

9. One or more non-transitory computer-readable media that include computer-readable instructions stored thereon that are executable by one or more processors to perform or control performance of operations comprising:

obtain data input including one or more words;

obtain a set of emotions;

determine a set of expressed emotions and a set of expressed emotion probabilities based on the one or more words, each expressed emotion of the set of expressed emotions corresponding to a different expressed emotion probability of the set of expressed emotion probabilities, each expressed emotion of the set of expressed emotions corresponding with a different emotion of the set of emotions;

obtain a set of likelihood probabilities, each likelihood probability of the set of likelihood probabilities corresponding to a conditional probability of an expressed emotion of the set of expressed emotions given an experienced emotion of a group of experienced emotions, each experienced emotion of the group of experienced emotions corresponding with a different emotion of the set of emotions;

determine a set of experienced emotions of the group of experienced emotions and a set of experienced emotion probabilities based on the set of expressed emotion probabilities and the set of likelihood probabilities, each experienced emotion of the set of experienced emotions corresponding to a different experienced emotion probability of the set of experienced emotion probabilities;

select an experienced emotion of the set of experienced emotions based on the selected experienced emotion corresponding to the highest experienced emotion probability of the set of experienced emotion probabilities; and in response to the selected experienced emotion being different from an expressed emotion of the set of expressed emotions corresponding to the highest expressed emotion probability of the set of expressed emotion probabilities, present the selected experienced emotion.

10. The non-transitory computer-readable media of claim 9, wherein the data input includes a text string.

11. The non-transitory computer-readable media of claim 9, wherein determining the set of expressed emotions and the set of expressed emotion probabilities comprises:

obtaining an emotion vocabulary including a plurality of emotion words related to each emotion of the set of emotions;

comparing the one or more words with the plurality of emotion words;

based on the comparing, identifying an expressed emotion probability for each emotion of the set of emotions;

identifying emotions of the set of emotions associated with an identified expressed emotion probability greater than zero as the set of expressed emotions; and identifying identified expressed emotion probabilities greater than zero as the set of expressed emotion probabilities.

12. The non-transitory computer-readable media of claim 9, wherein obtaining the set of likelihood probabilities comprises:

obtaining sentiment embeddings associated with the each emotion of the set of expressed emotions and the group of experienced emotions;

obtaining a similarity between each pair of emotions of the set of expressed emotions and the group of experienced emotions based on the sentiment embeddings; and normalizing the similarity between each pair of emotions to generate a conditional probability of an expressed emotion given an experienced emotion.

13. The non-transitory computer-readable media of claim 12, wherein determining the at least one experienced emotion comprises:

for each expressed emotion of the set of expressed emotions, generating an equation equating the expressed emotion probability associated with the expressed emotion to a sum of products of the conditional probability of the expressed emotion given each experienced emotion with the probability of the expressed emotion; and solving the generated equations to determine the set of experienced emotions and the set of experienced emotion probabilities.

14. The non-transitory computer-readable media of claim 13, wherein solving the generated equations includes solving the generated equations subject to a constraint of the sum of the set of experienced emotion probabilities equaling 1 and a constraint of each probability of the set of experienced emotion probabilities being non-negative.

15. The non-transitory computer-readable media of claim 9, further comprising providing counseling to the user.

16. The non-transitory computer-readable media of claim 9, wherein the set of emotions includes one or more of: happiness, sadness, anger, fear, surprise, worry, and trouble.

17. A system to estimate experienced emotions of a user, the system comprising:

one or more non-transitory computer-readable media that include computer-readable instructions stored thereon; and one or more processors communicatively coupled to the one or more computer-readable media, the one or more processors configured to, in response to execution of the instructions, perform or control performance of operations comprising:

obtain a set of emotions;

obtain data input from a user including one or more words;

determine at least one expressed emotion in the data input based on the one or more words, the at least one expressed emotion corresponding with emotions of the set of emotions;

obtain a set of emotion pairs, each emotion pair of the set of emotion pairs including an expressed emotion of the at least one expressed emotion, an experienced emotion corresponding with an emotion of the set of emotions, and a probability of the expressed emotion given the experienced emotion;

determine at least one experienced emotion based on the at least one expressed emotion and the set of emotion pairs; and in response to the at least one experienced emotion being different from the at least one expressed emotion, provide counseling to the user based on the at least one experienced emotion.

18. The system of claim 17, wherein determining at least one expressed emotion comprises:

obtaining an emotion vocabulary including a plurality of emotion words related to each emotion of the set of emotions;

comparing the one or more words of the data input with the plurality of emotion words;

based on the comparing, identifying an expressed emotion probability for each emotion of the set of emotions; and identifying emotions of the set of emotions associated with an identified expressed emotion probability greater than zero as the at least one expressed emotion.

19. The system of claim 17, the operations further comprising obtaining a diagnosis of a mental state of the user based on the at least one experienced emotion and based on the data input and wherein providing counseling to the user comprises identifying a treatment for the user based on the diagnosis.

20. The system of claim 17, wherein the set of emotions includes one or more of: happiness, sadness, anger, fear, surprise, worry, and trouble.

* * * * *